United States Patent
Freitas et al.

(10) Patent No.: US 9,393,259 B2
(45) Date of Patent: Jul. 19, 2016

(54) COMPOSITION COMPRISING ARABINOGALACTAN AND POLYPHENOLS FROM LARCH TREES

(71) Applicant: Lonza Ltd, Basel (CH)

(72) Inventors: Ulla Freitas, Lörrach (DE); Bryan Rodriguez, Spring Branch, TX (US)

(73) Assignee: Lonza Ltd., Basel (CH)

( * ) Notice: Subject to any disclaimer, the term of this patent is extended or adjusted under 35 U.S.C. 154(b) by 0 days.

(21) Appl. No.: 13/848,487

(22) Filed: Mar. 21, 2013

(65) Prior Publication Data

US 2014/0288021 A1    Sep. 25, 2014

(51) Int. Cl.
| | |
|---|---|
| *A01N 43/04* | (2006.01) |
| *A61K 31/715* | (2006.01) |
| *A61K 31/05* | (2006.01) |
| *A61K 31/716* | (2006.01) |
| *A61K 36/15* | (2006.01) |

(52) U.S. Cl.
CPC ............... *A61K 31/715* (2013.01); *A61K 31/05* (2013.01); *A61K 31/716* (2013.01); *A61K 36/15* (2013.01)

(58) Field of Classification Search
None
See application file for complete search history.

(56) References Cited

U.S. PATENT DOCUMENTS

| | | | |
|---|---|---|---|
| 5,614,501 A * | 3/1997 | Richards ........................ | 514/22 |
| 5,756,098 A | 5/1998 | Price et al. | |
| 6,087,092 A | 7/2000 | Richards | |
| 6,303,584 B1 | 10/2001 | Richards | |
| 6,767,546 B1 | 7/2004 | Allen et al. | |
| 8,784,844 B2 | 7/2014 | Rodriguez et al. | |
| 2014/0286997 A1 | 9/2014 | Rodriguez et al. | |

FOREIGN PATENT DOCUMENTS

| | | |
|---|---|---|
| JP | 2009256310 A | 11/2009 |
| JP | 2011526285 A | 10/2011 |
| RU | 2357746 C2 | 6/2009 |
| RU | 2421215 C1 | 6/2011 |
| WO | WO 97/21734 A1 | 6/1997 |
| WO | WO 99/15033 A | 4/1999 |
| WO | WO 2009/158395 A1 | 12/2009 |
| WO | WO 2011/038898 | 4/2011 |

OTHER PUBLICATIONS

"Prophylactic." Merrian-Webster.com. Merriam-Webster n. d. Wed. Jul. 16, 2014. <http: //Merriam-webster.com/dictionary/prophylactic>.*
Riede et al. Current Medical Research & Opinion (2013), vol. 29, pp. 251-258.*
Udani et al. Nutrition Journal (2010), vol. 9:32, http://www.nutritionj.com/contents/9/1/32 pp. 1-7.*
French et al. The Lancet (2000), vol. 355, pp. 2106-2111.*
Turner et al., Ineffectiveness of Echinacea for Prevention of Experimental Rhinovirus Colds, Antimicrobial Agents and Cehmotherapy, Jun. 2000, vol. 44, No. 6, p. 1708-1709.
Yale et al., Echinacea purpurea Therapy for the Treatment of the Common Cold, Arch Intern Med, vol. 164, 2004.
Classen et al., Characterization of an arabinogalactan-protein isolated from pressed juice of Echinacea purpurea by precipitation with the β-glucosyl Yariv reagent, Carbohydrate Research, 327 (2000) 497-504.
Adam A. et al., "Preparation and biological properties of water-soluble adjuvant fractions from delipidated cells of Mycobacterium smegmatis and Nocardia opaca," *Infection and Immunity*, 7:6:855-861, 1973.
Arifkhodzaev A.O., "Galactans and Galactan-containing polysaccharides of higher plants," *Chemistry of Natural Compounds*, 36:3:229-244, 2000.
Artz et al., "Pneumococcal vaccination and revaccination of older adults," Clinical Microbiology Review, 16(2):308-318, 2003.
Currier N.L. et al., "Effect over time of in-vivo administration of the polysaccharide arabinogalactan on immune and hemopoietic cell lineages in murine spleen and bone marrow," Phytomedicine, 10:145-153, 2003.
Database WPI Week 201166 Thomson Scientific, London, GB; AN 2011-G89620 XP002677598, & RU 2 421 215 C1 (DIOD Ecological Tech Stock CO) Jun. 20, 2011.
Database WPI Week 209975 Thomson Scientific, London, GB; AN 2009-Q91674 XP002677599, & JP 2009 256310 A (Hokkaido Mitsu Kagaku KK) Nov. 5, 2009.
Database WPI Week 209952 Thomson Scientific, London, GB; AN 2009-L07398 XP002677600, & RU 2 357 746 C2 (Goldbert YA S) Jun. 10, 2009.
Deloria-Knoll M. et al., "Effect of zinc and vitamin A supplementation on antibody responses to a pneumococcal conjugate vaccine in HIV-positive injection drug users: a randomized tiral," Vaccine, 24:1670-1679, 2006.
Dubrovina V I et al., "Comparative study of immunomodulating effects of natural experimental preparations on phagocytosis of Yersinia pseudotuberculosis," *Meditsinskaya Parazitologlia* I, *Parazitarnyea Bolezni*, 3:44-46, 2001.
Hauer J. et al., "Mechanism of stimulation of human natural killer cytotoxicity by arabinogalactan from Larix occidentalls," *Cancer Immunology and Immunotherapy*, 36:4:237-244, 1993.
Lamm S. et al., "Persistent response to pneumococcal vaccine in individuals supplemented with a novel water soluble extract of Uncaria tomentosa," *C-Med-100, Phytomedicine*, 8:4:267-274, 2001.
Marciani D. J., "Vaccine adjuvants: Role and mechanisms of action in vaccine immunogenicity," *Drug Discovery Today*, 8:20:934-943, 2003.
Kelly G.S., "Larch arabinogalactan: Clinical relevance of a novel immune-enhancing polysaccharide," Alternative Medicine Review, 4: 2:96-103, 1999.

(Continued)

*Primary Examiner* — Patrick Lewis
(74) *Attorney, Agent, or Firm* — Medler Ferro Woodhouse & Mills PLLC

(57) ABSTRACT

The present invention includes a composition and method of treatment having arabinogalactan and polyphenols from larch trees for the use in prophylactic treatment of upper respiratory tract infections. The invention also includes treatment using such composition.

13 Claims, No Drawings

(56) References Cited

OTHER PUBLICATIONS

Udani Jay K. et al., "Proprietary arabinogalactan extract increases antibody response to the pneumonia vaccine: a randomized, double-bind, placebo-controlled, pilot study in healthy volunteers," *Nutrition Journal*, 9:1-32, 2010.

Kim L.S. et al., "Immunological activity of larch arabinogalactan and Echinacea: a preliminary, randomized, double-blind, placebo-controlled trial," *Alternative Medicine Review*, 7:2:1:138-149, 2002.

Moriguti J.C. et al., "Effects of arginine supplementaion on the humoral innate immune response of older people," Eur J Clin Nutr, 59:1362-1366, 2005.

Roxas, M. et al., "Colds and influenza: A review of diagnosis and conventional, botanical, and nutritional considerations," Altern Med Rev, 12:25-48, 2007.

Sun, H.X. et al., "Novel polysaccharide adjuvant from the roots of Actinidia eriantha with dual TH1 and Th2 potentiating activity," *Vaccine*, 27:30:19:3984-3991, 2009.

Larex, Inc. "GRAS Notice for Arabinogalactan from the Eastern Larch Tree," pp. 1-327, 2001; and U.S. Food and Drug Administration Agency Response Letter GRAS Notice No. GRN 000084, pp. 1-4, 2002.

Talkington D F. et al., "Protection of mice against fatal pneumococcal challenge by immunization with pneumococcal surface adhesin A (PsaA)," Microb Pathog.1996;21:17-22.

Crick D.C. et al., "Biosynthesis of the arabinogalactan-peptidoglycan complex of *Mycobacterium tuberculosis*," Glycobiology, 11(9):107R-118R, 2001.

"Rest Aid." Lonza Brochures RestAid Supports Natural Immune Function <http://bio.lonza.com/uploads/tx_mwaxmarketingmaterial/Lonza_Brochures_ResistAid_Supports_Natural_Immune_Function.pdf>.

"Prophylactic." Merrian-Webster.com. Merriam-Webster n. d. Wed. Jul. 16, 2014. <http://Merriam-webster.com/dictionary/prophylactic>.

Non-Final Office Action for U.S. Appl. No. 12/894,266 (now U.S. Pat. No. 8,784,844) dated Jun. 17, 2011, Final Office Action for U.S. Appl. No. 12/894,266 (now U.S. Pat. No. 8,784,844) dated Jan. 5, 2012.

Final Office Action for U.S. Appl. No. 12/894,266 (now U.S. Pat. No. 8,784,844) dated Dec. 18, 2013.

International Search Report and the Written Opinion for International Application PCT/EP2010/005940, mailed Jan. 7, 2011.

International Search Report for PCT/EP2013/000854 mailed Aug. 8, 2013.

Boehme, L. et al, "Role of ResistAid™ in reducing the occurrence of the common cold," presented at World Immune Regulation Conference in Davos, Switzerland, Mar. 18-21, 2012.

Office Action for co-pending U.S. Appl. No. 14/299,490, mailed Aug. 3, 2015.

"Prevention of Pneumococcal Disease: Recommendations of the Advisory Committee on Immunization Practices (ACIP)", *MMWR Recommendations and Reports* 46:RR-08:1-24 (1997).

\* cited by examiner

COMPOSITION COMPRISING ARABINOGALACTAN AND POLYPHENOLS FROM LARCH TREES

The subject of the present invention is a composition comprising arabinogalactan and polyphenols from larch trees for the use in prophylactic treatment of upper respiratory tract infections.

BACKGROUND OF THE INVENTION

Each year, millions of people suffer from upper respiratory tract infections (URI or URTI) predominantly caused by virus infections. About 30 to 40% of cases are caused by rhinovirus infections. Other viruses include the coronavirus, para influenza virus, adenovirus and enterovirus. Another source of infection is bacterial attack, in part as second infection. URI involve the upper respiratory tract, i.e. nose, sinuses, pharynx or larynx and commonly include diseases such as tonsillitis (inflammation of the tonsils), otitis media, rhinitis (inflammation of the nasal mucosa), rhinosinusitis or sinusitis (inflammation of the nares and paranasal sinuses, including frontal, ethmoid, maxillary, and sphenoid), nasopharyngitis (rhinopharyngitis or the common cold, causing inflammation of the nares, pharynx, hypopharynx, uvula, and tonsils), pharyngitis (inflammation of the pharynx, hypopharynx, uvula, and tonsils), epiglottitis or supraglottitis, (inflammation of the superior portion of the larynx and supraglottic area), laryngitis—Inflammation of the larynx, laryngotracheitis (inflammation of the larynx, trachea, and subglottic area) and tracheitis (inflammation of the trachea and subglottic area). More than 200 rhinoviruses are known for causing URI. Depending from the area, the normal risk for developing URI ranges from less than 10 episodes per human individual per year in most industrialized countries up to several hundred episodes per human individual per year in some African an Asian countries. The overall risk in Central America, Africa and Asia, is at about 100 episodes. In some areas, predominantly at the eastern African coast and in Central Asia, the risk can reach a level of approx. 200 episodes per year or more.

Viruses and bacteria causing URI are mainly spread from person to person through airborne droplets that are sneezed out or coughed up by an infected person. In some cases, viruses and bacteria can be spread when a person touches an infected surface (e.g., doorknobs, countertops, telephones) and then touches parts of the body comprising mucous membranes such as nose, mouth, or eyes. As such, these diseases are most easily spread in crowded conditions such as schools. Although most people recover fully, URI borne sick days cause an enormous damage to the economy each year. Among high-risk populations, such as those with other medical conditions (such as diabetes or cancer) or a weakened immune system, seniors, or very young children, in rare cases even death can be a consequence of URI. Peak times for colds are at the start of school and kinder garden in the fall, in mid-winter, and again in early spring. In industrialized western countries having a high medical and hygiene standard children catch approximately up to 8 colds per year, adults catch roughly 4 colds per year, and seniors about 2 colds per year. Total number of URI episodes might be a little bit higher. People infected with an influenza or cold virus become contagious 24 hours after the virus enters the body (often before symptoms appear). Adults remain infectious (can spread the virus to others) for about 6 days, and children remain infectious for up to 10 days.

Common prevention means against URI's include simple frequent hand washing, general behavior such as coughing or sneezing into sleeves, and vaccinations, which are not recommended for children less than 6 months, people who have an egg or chicken protein allergy, an allergy to any of the ingredients of the vaccine, a history of allergic reactions to the flu vaccine, or in case of acute illness.

Thus, there is a need to provide further prevention means against URI's, preferably against rhinovirus infections and more preferably against common cold.

Arabinogalactan, for example from Echinacea or larch, have been reported by Yale et al. (*Arch. Intern. Med.* 2004, 164, 1237-1241) and Turner et al. (AAC, 2000, 44, 1708-1709) to stimulate the immune system without reference to consequences to real diseases.

Nothing in the state of the art indicates that an arabinogalactan extract from larch is capable of effectively reduce the risk in catching an URI, preferably a disease caused by a rhinovirus or more preferably a common cold in real subjects.

Arabino galactane (also referred to arabinogalactan, larch arabinogalactan, galactoarabinin, larch fiber or larch gum; CAS: [9036-66-2]), is a highly branched polysaccharide having a molecular weight between 15000 to 60000 Daltons that is composed of galactose units and arabinose units (arabinogalactan) in the approximate ratio of 6:1 (Scheme 1). Expediently, the botanical source is from *Larix laricina* (eastern larch) or *Larix occidentalis* (western larch). Arabinogalactan from larch usually contains a certain amount of polyphenols. Typically polyphenols are present at approx. 1 to 4 wt-%, more preferably at approx. 2 wt-%. Larch arabinogalactan is approved by the United States Food and Drug Administration (FDA) as a GRAS (Generally Recognized As Safe) affirmed direct food additive. A commercially available form of arabinogalactan is ResistAid™, which is an extract from larch bark and/or wood (chips or sawdust) (*Larix* ssp.)

Structural formula:

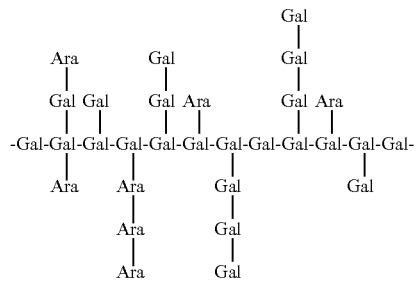

Scheme 1: Chemical structure of arabinogalactan in ResistAid™

Ara = Arabinose
Gal = Galactose

DISCLOSURE OF THE INVENTION

The technical problems laid out above are surprisingly solved by using a composition containing arabinogalactan for enhancing the adaptive immune response in subjects as defined in the claims.

We could demonstrate for the first time that daily administration of a composition comprising arabinogalactan and polyphenols from larch trees can effectively be used in prophylactic treatment of upper respiratory tract infections.

"Subjects" according to the claims are vertebrates, preferably mammals and birds, more preferably humans, swine, poultry, beef cattle, dogs, cats, goats and horses, most preferably humans.

"Arabinogalactan" according to the invention is to be understood as relating to any compound that is composed of galactose units and arabinose units in the approximate ratio of 100:1 to 1:1, preferably 6:1, Specifically, arabinogalactan according to the invention is preferably characterized by having a backbone of 2(1→3)-linked β-D-galactopyranosyl units, each of which bears a substituent at the C-6 position. Most of these side chains are galactobiosyl units containing a (1→6)-β-D-linkage as well as α-L-arabinofuranosyl units. However, the scope of the present invention also encompasses arabinogalactan derivatives, e.g. where arabinogalactan is in covalent association with varying amounts of protein (arabinogalactan-proteins (AGPs) as described in Classen et al., *Carbohydrate Research*, 2000, 327, 497-504). Other derivatives include quaternized or lipidated forms of arabinogalactan.

According to the invention, preferably arabinogalactan and polyphenols from larch trees are derived from larch trees (*Larix* spp.), especially from *larix laricina* (eastern larch) or *Larix occidentalis* (western larch).

The invention includes a composition having arabinogalactan and polyphenols from larch trees, and the use of such composition in prophylactic treatment of upper respiratory tract infections.

The invention further includes a composition having arabinogalactan and polyphenols from larch trees and the use of such composition in prophylactic treatment of diseases caused by rhinoviruses.

Also the invention includes a composition having arabinogalactan and polyphenols from larch trees and the use of such composition in prophylactic treatment of common cold.

In accordance with the upper mentioned diseases we also furthermore claim a composition for the use in prophylactic long term treatment of diseases selected from the group consisting of upper respiratory tract infections, diseases caused by rhinoviruses and common cold.

A composition according to any of claims 1 to 3, having prophylactic effects in enhancing resistance against diseases selected from upper respiratory tract infections, diseases caused by rhinoviruses and common cold.

In a preferred embodiment the composition mentioned above, said compositions comprising arabinogalactan and polyphenols from larch trees, can be used for treatment of subjects having increased risk for catching a disease selected from upper respiratory tract infections, diseases caused by rhinoviruses, and common cold, in order to reduce of number of disease events compared to untreated subjects.

Subjects with increased risk for catching a common cold in the meaning of the invention are for example people standing in highly infectious areas, people lacking sleep, or people having a weakened immune system. More specifically, such subjects with increased risk are for example elder people of 65 years old or older, people living in a nursing home or chronic care facility, patients having lung diseases (e.g. asthma, chronic obstructive pulmonary disease), patients having low heart conditions (e.g. angina, congestive heart failure), patients having diabetes, other metabolic diseases, kidney problems, blood disorders (e.g., anemia), having been diagnosed as suffering from morbid obesity or generally having a weakened immune system (e.g., are taking steroid medications, have cancer, or have HIV) and patients at high risk for complications, further people which are traveling to areas where URI are common, children aged 6 months to 23 months, or aged 6 months to 18 years and are taking long-term medical therapy, healthy children at 2 to 4 years of age, further people working in healthcare, such as doctors, nurses, and pharmacists. Increased risk for animals occurs in large-scale or intensive livestock farming. People working in or living nearby such animals are also potentially affected where viruses can be transferred from animal to human and vice versa.

In another preferred embodiment the composition mentioned above, said compositions comprising arabinogalactan and polyphenols from larch trees, can be used for treatment of subjects having increased susceptibility for catching a disease selected from upper respiratory tract infections, diseases caused by rhinoviruses, and common cold, in order to reduce the number of disease events compared to untreated subjects.

Subjects with increased susceptibility for URI are people from the group mentioned above which already suffer from at least one other disease and/or having a suboptimal health status.

In general, people with increased risk and/or susceptibility for catching a disease selected from upper respiratory tract infections, diseases caused by rhinoviruses, and common cold, preferably for catching a common cold, develop at least 3 common colds within 6 month in untreated status, preferably, children, such as infants, young children, school kids, people with sleeping difficulties or sleep deficits, stressed people, older people, people with poor nutritional status.

The instant composition comprising arabinogalactan and polyphenols from larch trees, for example commercially available ResistAid™ from Lonza (Switzerland), should be administered on a daily basis.

Expediently, the administration of the composition above starts prior to peak cold season in spring and/or autumn, preferably starts 30 days prior to peak cold season, more preferably 60 days prior to peak cold season. In general, preferably the instant composition shall be administered as long term administration for at least 30 days, more preferably for at least 60 days, even more preferably for at least 12 weeks.

The instant composition expediently is administered in liquid or solid form. It can be mixed with food and feed and any kind of beverage.

To reach a prophylactic effect the instant composition should be administered in a daily amount of approx. 0.5 g to 15 g per subject, more preferably in an amount of 1.0 g to 7 g. Exceeding 15 g daily has no adverse effect on health on subjects, especially not in humans. Preferably treatment is carried out with 1.5 g to 4.5 g daily, most preferred at least 1.5 g daily. In another preferred embodiment the daily dose is administered up to 3 times daily, more preferably each dose at approx. 1.5 g of the composition.

We also claim the use of a composition comprising arabinogalactan and polyphenols from larch trees for preventing development of common cold.

Further claimed is the use of a composition above for the manufacture of a medicament, preferably a medicament for preventing a disease selected from the group consisting of upper respiratory tract infections, diseases caused by rhinoviruses, and common cold.

We also claim the use of a composition comprising arabinogalactan and polyphenols from larch trees for the manufacture of a nutritional product. The nutritional product can be selected from the group consisting of foods, food additives, food supplements, feeds, feed additives and feed supplements, each suitable directly or indirectly for use in a method for treatment of the human or animal body to proactively prevent development of upper respiratory tract infections. Nutritional products also comprise functional beverages, functional foods such as bars, breakfast cereals etc. or as dietary supplements such as capsules, tablets, liquids (offered for example in ampules/phials), dry powder, blends or premixes.

Finally, also claimed is a method for prophylactic treatment of a disease selected from the group consisting of upper respiratory tract infections, diseases caused by rhinoviruses, and common cold, characterized in administrating a composition arabinogalactan and polyphenols from larch trees as mentioned above.

EXAMPLES

The instant invention will be further described in the following, non-limiting examples and study outcomes.

Example 1

Double-Blind Study 1.1 Study Objective

The goal of this double-blind, randomized, placebo-controlled multi-center clinical study conducted by analyse&realize (a&r, Berlin, Germany) was to demonstrate the prophylactic effect of ResistAid™ in subjects with increased susceptibility to upper respiratory tract infections.

Primary end point was the reduction of number of cold episodes in comparison between ResistAid™ and placebo study arms.

Secondary end points were the reduction of episode duration and episode intensity.

Safety and further parameters included the global evaluation of efficacy and tolerability assessed by both the investigators and the subjects and the assessment of adverse events, safety laboratory parameters, special laboratory parameters (leukocyte differentiation) and eating habits.

1.2 Study Subjects

The full analysis set (FAS) population consisted of 199 subjects, 12 subjects were excluded from the per protocol (PP) set resulting in 187 subjects. All subjects were healthy at the beginning and at the end of the study, as ascertained by physical examination as well as blood analysis.

1.3 Study Design

The clinical study was directed to be applicable to subjects with increased susceptibility to upper respiratory tract infections.

During the study period of 12 weeks, 101/97 subjects (FAS/PP) had to take investigational study product (ResistAid™) and further 98/90 subjects (FAS/PP) placebo (Maltodextrin) once daily. The subjects were instructed to dissolve the content of a sachet with the investigational product (4.5 g of powder) in approx. 100 to 150 mL of liquid and take the prepared drink at breakfast. All other eating habits were kept unchanged.

A total of 3 basic visits were performed: Visit 1 at study start (=baseline), Control Visit after 6 weeks and Termination Visit after 12 weeks. Additionally, an Episode Visit was performed at start and on the 5th day of each cold episode. The exact day of the cold episode was recorded in the CRF.

Between Visit 1 and the Control Visit as well as between Control Visit and the Termination Visit, one or more cold episodes could occur. During an episode, the subjects recorded and assessed their cold symptoms in the subject diary, for a period of 14 days. The diaries were checked by the investigators at the second Episode Visit of each visit.

At study end (Termination Visit), the investigators and the subjects assessed the global efficacy and tolerability of the investigational product. At the start and end of the study, subjects recorded their eating habits in a diet diary. Further, the safety laboratory parameters as well as special laboratory parameters (leukocyte differentiation) were assessed.

The investigators handed out the investigational product including a back-up quantity for 8 additional days to the subjects at Visit 1 and Control Visit, respectively. The unused sachets were returned to the investigators at both the Control and the Termination Visit for compliance assessment.

1.4 Analyses

The primary endpoint was defined as the reduction of the number of cold episodes after 12-week study period in verum group compared to placebo. Thus, the primary parameter was the number of cold episodes NumberCE.

Therefore the statistical null hypothesis H0 implied the statement that there is no difference between the mean number of cold episodes of both groups, thus to following can be made:

H0: NumberCE (verum)=NumberCE (placebo)

The null hypothesis was to be tested as opposed to the alternative hypothesis HA HA: NumberCE (verum)≠NumberCE (placebo) (two-tailed test)

and

HA: NumberCE (verum)<NumberCE (placebo) (one-tailed test), respectively.

The non-parametric Mann-Whitney U test had to be used so that this hypothesis could be proven by the rank sums. All tests were to be performed with a significance level (type I error) of 5.0% (two-tailed test) or of 2.5% (one-tailed test).

Secondary endpoints (reduction in duration and intensity of individual cold episodes) and safety and further parameters (global assessment of efficacy and tolerability, number of AEs, laboratory parameters and eating habits) should be evaluated primarily by using non-parametric procedures. Mann-Whitney U test should be used for between-groups comparison and Wilcoxon test for within-group (pre/post) comparison. Further, Friedman test should be used for comparison of dependent samples and Chi2 test for assessment of proportional values. In case of small samples size (e.g. subgroups) exact tests should be used. Parametric procedures supplement the analysis if the scale of the observed values justifies this kind of test.

The condition of normal distributed values was not to be checked but discrepancy between non-parametric and parametric, if occurred, should be discussed.

All primary and secondary endpoints as well as safety and other variables were descriptively assessed in addition to an explorative examination. For the metric data (continuous data) the statistical characteristics are given (number, mean, standard deviation, median, extremes, and quartiles). For ordinal data (discrete data) the frequency distributions were performed. All nominal data (categorical data) are summarized using frequency tables. Where appropriate, the values of metric data were merged into ordinal classes according to clinical criteria to determine their frequency distribution. Data collected at repeated visits were examined using methods of multivariate analysis with repeat measurements.

Laboratory parameters should be evaluated as metric parameters; additionally the deviations from the reference ranges should be evaluated.

All tests should be performed with a significance level (type I error) of 5.0% (two tailed test) or of 2.5% for the one-tailed test at 80% power. 95% confidence intervals should be determined.

All p-values from statistical tests in connection with the explorative analyses that exceed the testing of the primary endpoint should be described tentatively.

All statistical analyses should be performed on the full analysis set population (FAS). At least for the primary end point an additional analysis should be performed in the valid case analysis set (VCAS). The results of both populations should be compared and any differences discussed.

The FAS population consists of all subjects who received at least one dose of investigational product (intent to treat). The VCAS population consists of all subjects from the FAS group who completed the clinical investigation according to the clinical investigation plan (CIP) with no major protocol violations. The assignment to the FAS and the VCAS population should be performed before unblinding the data. Analyses of any subgroups based on further criteria may be performed as appropriate, applying the above rules stated for the planned statistical analyses.

For the assessment of episodes, it should be considered that the observed values could be independent (episodes from different subjects) and dependent (episodes of the same subject). Thus, parameters related to an episode could be analyzed either based on the number of affected subjects (regardless of the number of episodes per subject) or based on the number of episodes (regardless if a subject had more than one episode); the respective basis of the analyses should be stated.

1.5 Results

In total, 191 cold episodes were documented in the CRF, affecting a total of 132 subjects (66.3% of 199 subjects). Thereof, 3 episodes were regarded as invalid as preceded by a flu vaccination (symptoms similar to common cold).

Thus, a total of 188 episodes, affecting 130 subjects (65.3%) were analyzed. There was a difference between the study arms regarding the number of subjects affected by a cold episode: V-group 58.4% (59 of 101) vs. P-group 72.4% (71 of 98); pChi=0.038.

Taking into account all episodes (including those preceded by a flu vaccination), a total of 191 episodes, affecting 132 subjects were analyzed. There was a difference between the study arms regarding the number of subjects affected by a cold episode: V-group 60.3% (61 of 101) vs. P-group 72.4% (71 of 98); pChi=0.072.

1.6 Efficacy Endpoints

Intake of ResistAid™ resulted in a reduced mean number of cold episodes (PP set-verum: 0.85±0.82 vs. placebo: 1.10±0.85; Pu=0.040). The total number of episodes showed a statistically significant difference in the ResistAid™ group compared to the placebo group (PP set-verum: 82 [n=97] vs. placebo: 99 [n=90]).

The percentage of subjects who suffered from one or more episodes was significantly higher in the placebo compared to the active group (PP set-verum: 59.8% vs. placebo: 74.4%, PChi=0.033).

1.7 Conclusions and Discussion

This randomized, double-blind, placebo-controlled, parallel-group study showed that consumption of ResistAid™ was associated with a significant reduction of the number of common cold episodes in comparison with placebo. Only approx. 25% of the untreated subjects didn't develop a cold, whereas approx. 40% of the treated subjects didn't develop a cold. Thus, the number of subjects which didn't develop a cold was increased by 63%. The supplementation of the arabinogalactan preparation reduced the number of common cold episodes by 23%, which indicates the potential of ResistAid™ to modulate the immune response to invading pathogens. The present study demonstrated an excellent safely profile of ResistAid™.

1.8 Safety

During the study period of 12 weeks, a total of 3 basic visits were performed: Visit 1 (study start), Control Visit (at 6 weeks) and Termination Visit (at 12 weeks). Additionally, Episode Visits were scheduled at start and on the 5th day of each cold episode. The number of Episode Visits per subject varied, depending on the number of episodes occurred during the study.

During an episode, the subjects recorded and assessed their cold symptoms in the subject diary, for a period of 14 days. At Termination Visit, the investigators and the subjects assessed the global efficacy and tolerability of the investigational product. At the start and end of the study, subjects recorded their eating habits in a diet diary and the safety laboratory parameters/special laboratory parameters (leukocyte differentiation) were assessed. Use of analgesics and antibiotics was recorded in the CRF and the subject diary. Any episodes treated with antibiotics were not included in the evaluation of the relevant variables.

1.9 Abbreviations
CRF Case Report Form
FAS Full analysis set
GRAS Generally Recognized As Safe
P Placebo
pChi Chi2 test p value
PP per protocol (completed study)
Pu Mann-Whitney U test p value
URI or URTI Upper respiratory tract infections
V Verum; Visit
VCAS Valid Case Analysis Set Example 2

Simplified Test Study

10 Healthy subjects were instructed to dissolve the content of a 1.5 g sachet of the investigational product in approx. 50 mL of liquid and take the prepared drink once daily. Although the sample group was small, a reduction of cold episodes could also be observed in view of the placebo group of example 1.

Thus, while there have been described what are presently believed to be the preferred embodiments of the present invention, those skilled in the art will appreciate that changes and modifications may be made thereto without departing from the spirit of the invention, and it is intended to claim all such changes and modifications as fall within the true scope of the invention as set forth in the following claims.

The invention claimed is:

1. A method for reducing the number of upper respiratory tract infections in a subject having an increased susceptibility for an upper respiratory tract infection, the method comprising administering to the subject a composition comprising arabinogalactan and polyphenols from larch trees, wherein the composition comprises from about 1% (w/w) to about 4% (w/w) of polyphenols relative to a total amount of arabinogalactan and polyphenols in the composition, wherein the subject having an increased susceptibility for an upper respiratory tract infection develops at least three (3) episodes of an upper respiratory tract infection within six (6) months in untreated status.

2. The method of claim 1, wherein the subject is a human subject.

3. The method of claim 1, wherein the composition is administered to the subject on a daily basis.

4. The method of claim 3, wherein the composition is administered to the subject for at least 30 days.

5. The method of claim 1, wherein the composition is administered to the subject in a daily amount equivalent to about 0.5 g to about 15 g of the arabinogalactan and polyphenols.

6. The method of claim 1, wherein the composition is administered to the subject in an amount of at least about 1.5 g per day.

7. The method of claim 1, wherein the composition is administered to the subject with a food or a beverage.

8. The method of claim 1, wherein the subject has a weakened immune system.

9. The method of claim 1, wherein the subject has a medical condition selected from lung disease, a heart condition, a metabolic disease, a kidney problem, a blood disorder, morbid obesity, cancer, or HIV; or wherein the subject is taking a steroid medication.

10. The method of claim 2, wherein the subject is selected from a subject being 65 years or older, and a subject aged six months to 4 years.

11. The method of claim 1, wherein the upper respiratory tract infection is caused by a rhinovirus.

12. The method of claim 1, wherein the upper respiratory tract infection is a common cold.

13. The method of claim 1, wherein said administering reduces the number of common cold episodes in the subject when compared to subjects not being administered the composition.

* * * * *